US00PP30436P2

(12) United States Plant Patent
Van Swieten

(10) Patent No.: US PP30,436 P2
(45) Date of Patent: Apr. 23, 2019

(54) ***PHALAENOPSIS* ORCHID PLANT NAMED 'PHALGEXPA'**

(50) Latin Name: ***Phalaenopsis* hybrid**
Varietal Denomination: PHALGEXPA

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,966

(22) Filed: Jan. 19, 2018

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALGEXPA', particularly characterized by having light purple flowers with a purple blush and red-purple lip, 1 to 3 peduncles that are long and moderate, leaves that are oblong, and is propagated by meristem tissue culture, is disclosed.

3 Drawing Sheets

Genus and species: *Phalaenopsis* hybrid.
Variety denomination: 'PHALGEXPA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGEXPA'.

The new *Phalaenopsis* plant is a product of a planned breeding program conducted by the inventor in Bleiswijk, The Netherlands. The objective of this breeding program was to create a new *Phalaenopsis* plant with numerous attractive and unique light purple flowers with a purple blush and red-purple lip, suitable for potted plant production.

The new *Phalaenopsis* plant 'PHALGEXPA' is a result of cross-pollination made by the inventor in June 2009 in Bleiswijk, The Netherlands of the proprietary female, or seed parent, *Phalaenopsis* hybrid '23426-01' (unpatented) with the proprietary male, or pollen parent, *Phalaenopsis* hybrid '4347-01' (unpatented).

The new *Phalaenopsis* was selected by the inventor as a single plant within the progeny of the stated cross-pollination in a controlled greenhouse in Bleiswijk, The Netherlands in June 2012. Asexual reproduction of the new *Phalaenopsis* plant by meristem tissue culture since 2015 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGEXPA' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGEXPA' as a new and distinct variety of *Phalaenopsis* plant.

1) Light purple flowers with a purple blush and red-purple lip;
2) 1 to 3 peduncles;
3) Peduncle is long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, bud and foliage of the plant; the colors shown are as true as can be reasonably obtained by conventional photographic procedures. The photographs were taken in a greenhouse in Bleiswijk, The Netherlands, from 50-week old plants in November 2017. Colors in the photographs may differ from the color values cited in the detailed botanical description, which accurately describe the actual colors of the new variety.

DESCRIPTION OF THE NEW VARIETY

Figure 1:
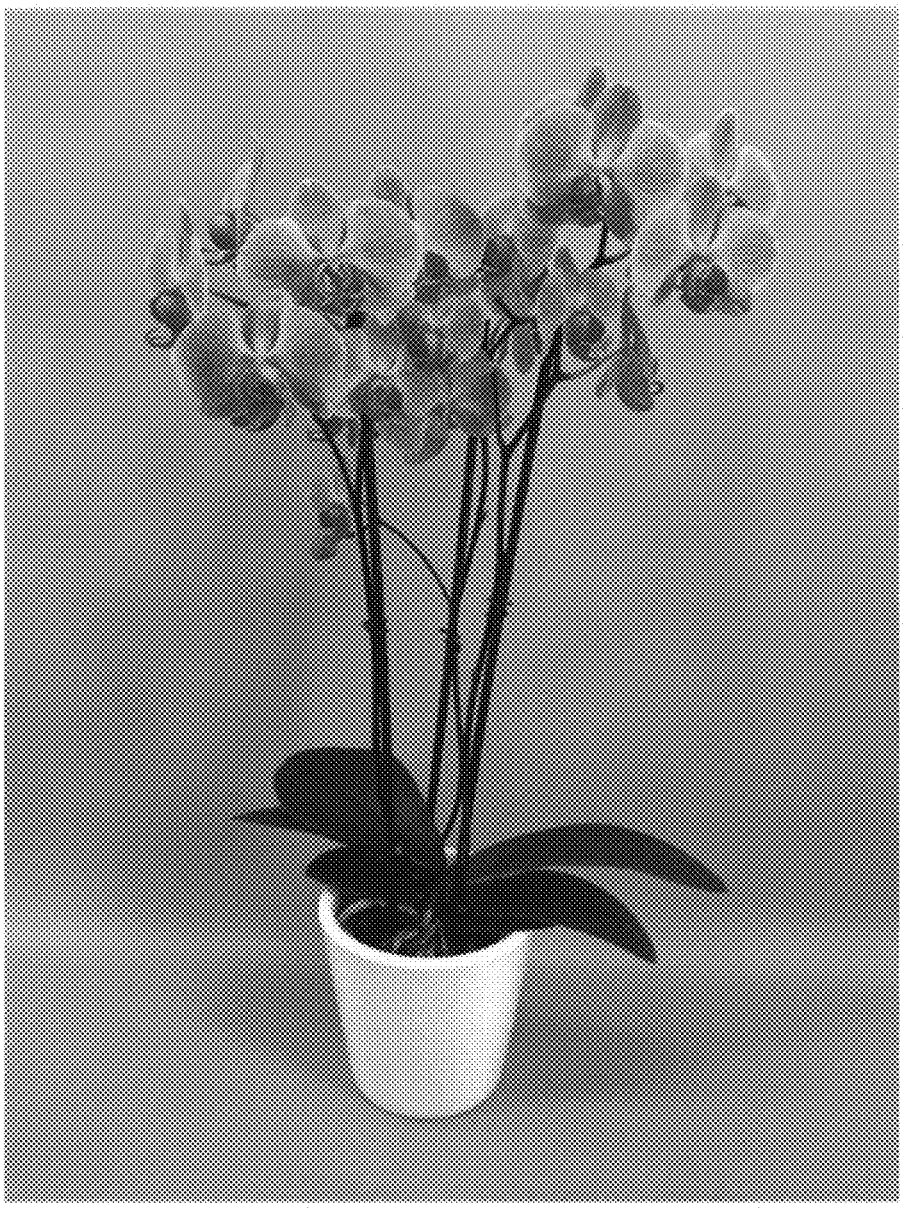
FIG. 1 shows the overall plant habit, including blooms, bud and foliage of 'PHALGEXPA'.
Figure 2:
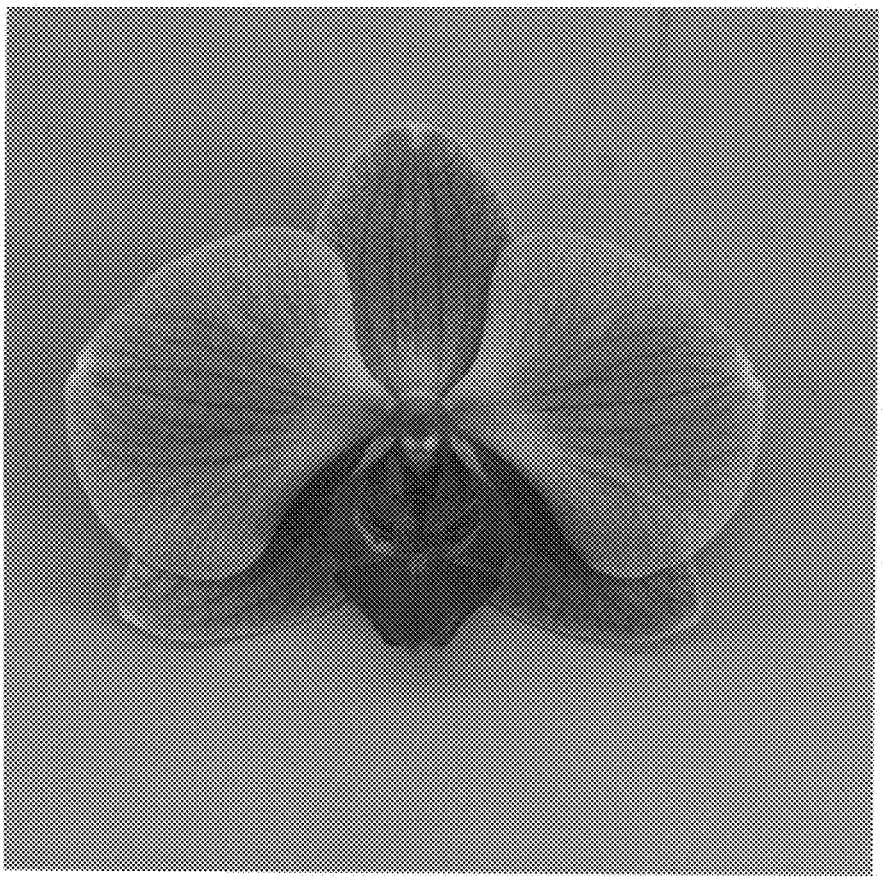
FIG. 2 shows a close-up of a flower of 'PHALGEXPA'.
Figure 3:
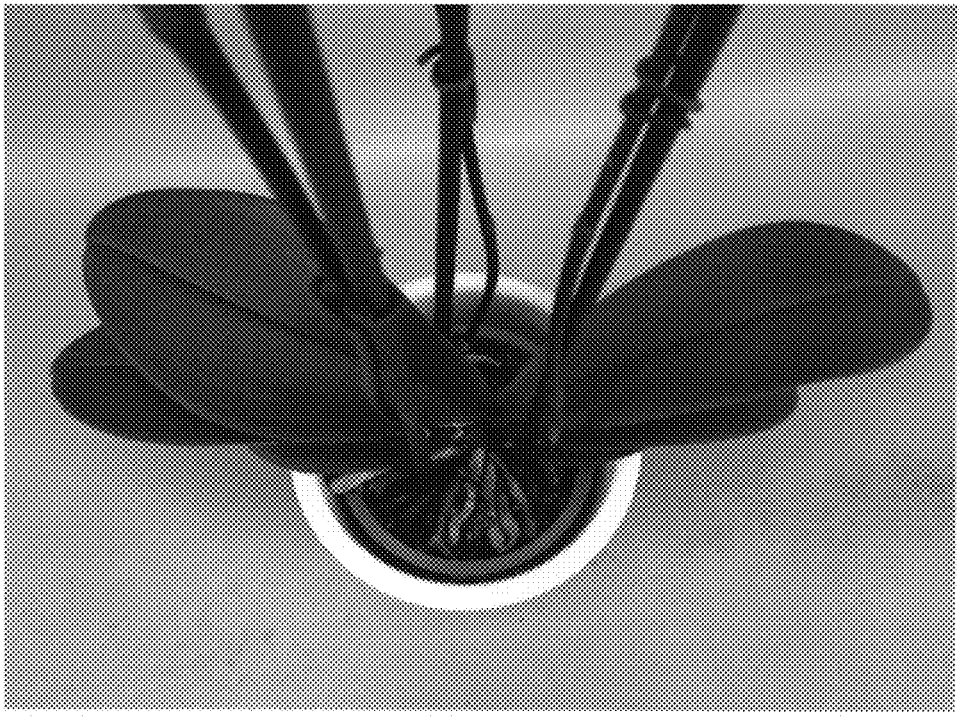
FIG. 3 shows an overhead view of the leaves of 'PHALGEXPA'.

The following detailed description sets forth the distinctive characteristics of 'PHALGEXPA'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in November 2017 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGEXPA'.

Parentage:

*Female parent*.—*Phalaenopsis* cultivar '23426-01' (unpatented).

*Male parent*.—*Phalaenopsis* cultivar '4347-01' (unpatented).

Propagation:

*Type*.—Meristem tissue culture.

Roots:

*Root description*.—Greyed-green colored roots (RHS 194C) with branching lateral roots having greyed red-purple colored root tips (RHS 185C).

Plant:

*Commercial crop time to flowering*.—Following asexual propagation (in-vitro), the rooted cuttings grow for 20-24 weeks. After transplantation in 12 cm pots, the plants are finished after 48 to 50 weeks.

*Growth habit of peduncle*.—Standard, green leaves, panicle.

*Height (from soil level to top of inflorescence)*.—Approximately 48.0 cm to 53.0 cm.

*Width (measured from leaf tips)*.—About 36.0 cm to 38.0 cm.

*Vigor*.—Moderate.

Leaves:

*Mature leaves*.—Quantity per plant: 6 to 8 leaves are produced before flowering. Length (fully expanded): 18.0 cm to 19.0 cm. Width: 7.5 cm to 8.5 cm. Shape: Oblong. Base shape: Moderately elongated. Apex: Obtuse unequal. Leaf blade angle with the petiole (measured from the horizontal position): Between 25 degrees and 35 degrees. Leaf margin: Entire. Color: Upper surface: RHS 147A. Lower surface: RHS 147B. Texture: Rough. Thickness: 2.2 mm to 2.6 mm. Venation: Pattern: Parallel. Color of the midvein: Upper surface: RHS 147A. Lower surface: RHS 147B with edge RHS 187A.

Peduncle:

*Quantity per plant*.—1 to 3.

*Number of flowers per peduncle*.—8 to 12.

*Length*.—48.0 cm to 53.0 cm.

*Diameter*.—4.0 mm to 4.4 mm.

*Strength*.—Moderate.

*Aspect*.—Upright to slightly pendant.

*Texture*.—Smooth.

*Color*.—Brown (RHS 200A) with a touch of light green (RHS 195A).

*Internode length*.—5.5 cm to 6.5 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 230.0 mm to 270.0 mm.

*Flowering time*.—First flowers can be expected 10 to 11 months after planting in a 12 cm (diameter) pot.

*Flower*.—Height: 75.0 mm to 80.0 mm. Diameter: 90.0 mm to 95.0 mm. Depth of lip: 25.0 mm to 27.0 mm.

*Flower longevity*.—On the plant: 12 to 18 weeks.

*Fragrance*.—Absent.

*Flower bud*.—Length: 23.0 mm to 25.0 mm. Width: 19.0 mm to 21.0 mm. Shape: Egg shaped. Color: Red-purple (RHS 72B and N77B) and light green (RHS 145C) at the base.

*Petals*.—Arrangement: Open/free. Shape: Semi-circular. Apex: Emarginated asymmetric. Margin: Entire. Length (from base to tip): 42.0 mm to 44.0 mm. Width: 50.0 mm to 52.0 mm. Color (when fully opened): Upper surface: Basic color: Light red-purple (RHS N78D). Over color: Light purple (RHS N78C). Lower surface: Basic color: Light red-purple (RHS N78D). Over color: Light purple (RHS N78C) at the base with light purple (RHS N78C) stripes.

*Dorsal sepal*.—Shape: Elliptic. Apex: Rounded to slightly emarginated. Margin: Entire. Length (from base to tip): 40.0 mm to 42.0 mm. Width: 31.0 mm to 33.0 mm. Color (when fully opened): Upper surface: Basic color: Light purple (RHS N78B). Over color: Slightly light red-purple (RHS N78D) at the base. Lower surface: Basic color: Light purple (RHS N78C). Over color: Purple-red region (RHS 72B) in the middle.

*Lateral sepals*.—Shape: Ovate. Apex: Obtuse asymmetric. Margin: Entire. Length (from base to tip): 41.0 mm to 43.0 mm. Width: 28.0 mm to 30.0 mm. Color (when fully opened): Upper surface: Basic color: Red-purple (RHS N78B). Over color: Light green (RHS 145C) at the base; dotted (RHS 71A) at the base. Lower surface: Basic color: Light purple (RHS 72B). Over color: Light green (RHS 145C) and slightly light purple (RHS N78C) at the base.

*Labellum (lip)*.—Whiskers: Present. Length of whiskers: 15.0 mm to 17.0 mm. Color of whiskers: Dark red-purple (RHS N79C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 23.0 mm to 25.0 mm. Width: 20.0 mm to 22.0 mm. Color: White (RHS NN155C) and slightly yellow (RHS 10B) with a few red stripes (RHS 185A) at the base; red (RHS 185A) and red-purple (RHS N78B) toward the margin.

*Apical lobe*.—Shape: Triangular. Margin: Entire. Length: 23.0 mm to 25.0 mm. Width: 20.0 mm to 22.0 mm. Color: Deep red (RHS 185A) and slightly yellow (RHS 10B) at the base; red-purple toward whiskers (RHS N78B).

*Callus*.—Average size: Medium. Height: 6.0 mm to 7.0 mm. Length: 6.0 mm to 7 0 mm. Width: 4.0 mm to 5.0 mm. Color: Yellow (RHS 14A), dotted (RHS 183B/C).

Reproductive organs:

*Column*.—Length: 8.0 mm to 9.0 mm. Diameter: 5.6 mm to 5.9 mm. Color: Red-purple (RHS N78B) at the base and (RHS N78A) toward the tip.

*Pollinia*.—Quantity: 2. Diameter: 0.9 mm to 1.2 mm. Color: Orange (RHS 25A).

*Ovary*.—Length: 16.0 mm to 18.0 mm. Diameter: 2.2 mm to 2.4 mm.

*Pedicel*.—Length: 35.0 mm to 40.0 mm. Diameter: 2.7 mm to 2.9 mm. Color: Mix of green (RHS 196B) and diluting dark red-purple (RHS N79B) at the base; light red-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGEXPA' differs from female parent plant '23426-01' (unpatented) in that 'PHALGEXPA' has dark red-purple whiskers, whereas '23426-01' has whiskers with purple at the base, light purple toward the tip and a yellow tip. Additionally, 'PHALGEXPA' has larger flowers and shorter whiskers than '23426-01'.

'PHALGEXPA' differs from male parent plant '4347-01' (unpatented) in that 'PHALGEXPA' has dark red-purple whiskers, whereas '4347-01' has deep red whiskers. Additionally, 'PHALGEXPA' has larger flowers and longer whiskers than '4347-01'.

'PHALGEXPA' is most similar to the commercial *Phalaenopsis* plants named 'PHALCIMEI' (U.S. Plant Pat. No. 27,200) and 'PHALDESBIM' (U.S. Plant Pat. No. 27,671). 'PHALGEXPA' differs from the commercial variety 'PHALCIMEI' in that 'PHALGEXPA' has light purple flowers, whereas 'PHALCIMEI' has purple flowers. Additionally, 'PHALGEXPA' has smaller flowers, narrower petals, and shorter whiskers than 'PHALCIMEI'.

'PHALGEXPA' differs from the commercial variety 'PHALDESBIM' in that 'PHALGEXPA' has light purple flowers, whereas 'PHALDESBIM' has purple flowers. Additionally, 'PHALGEXPA' has larger flowers and narrower petals than 'PHALDESBIM'.

I claim:

1. A new and distinct variety of *Phalaenopsis* plant named 'PHALGEXPA', substantially as described and illustrated herein.

* * * * *